(12) United States Patent
Segina et al.

(10) Patent No.: US 9,555,169 B2
(45) Date of Patent: *Jan. 31, 2017

(54) APPARATUS FOR HARVESTING IMPROVED BONE GRAFT MATERIAL UTILIZING AN IMPLANTABLE BIODEGRADABLE FILTER

(71) Applicants: Daniel Nick Segina, Satellite Beach, FL (US); James Arthur Proctor, Jr., Indialantic, FL (US)

(72) Inventors: Daniel Nick Segina, Satellite Beach, FL (US); James Arthur Proctor, Jr., Indialantic, FL (US)

(73) Assignee: Genesis Medical Devices, LLC, Melbourne Beach, FL (US)

( * ) Notice: Subject to any disclaimer, the term of this patent is extended or adjusted under 35 U.S.C. 154(b) by 52 days.

This patent is subject to a terminal disclaimer.

(21) Appl. No.: 14/305,049

(22) Filed: Jun. 16, 2014

(65) Prior Publication Data

US 2014/0363403 A1 Dec. 11, 2014

Related U.S. Application Data

(63) Continuation of application No. 13/091,123, filed on Apr. 21, 2011, now Pat. No. 8,790,321.
(Continued)

(51) Int. Cl.
*A61M 1/00* (2006.01)
*A61B 17/16* (2006.01)
(Continued)

(52) U.S. Cl.
CPC .......... *A61M 1/0056* (2013.01); *A61B 10/025* (2013.01); *A61B 17/1635* (2013.01);
(Continued)

(58) Field of Classification Search
CPC ... A61K 35/28; A61B 17/1635; A61B 10/025;
A61B 10/0283; A61B 17/1604; A61B 17/1644; A61B 17/1659; A61B 2010/0258; A61B 2017/1602; A61B 17/1622; A61B 2017/00969; A61B 2017/00004; A61M 1/0001; A61M 1/0056; A61M 2202/0014; A61M 2202/005; A61M 1/3693; A61M 1/3695; A61M 2202/10; A61M 2205/7545; A61M 2205/75; A61M 1/0064; A61M 2202/0021; A61M 2202/095; A61M 2210/02; A61F 2002/2835; A61F 2002/2842; A61F 2/4644; A61F 2002/4645; A61F 2002/4648; A61L 2430/02

See application file for complete search history.

(56) References Cited

U.S. PATENT DOCUMENTS 5,354,291 A * 10/1994 Bales ................ A61M 1/0045
604/22
5,505,716 A * 4/1996 Simmet ................ A61D 19/04
600/34

(Continued)

OTHER PUBLICATIONS

Synthes Ltd. "Reamer/Irrigator/Aspirator (RIA). For intramedulary reaming and bone harvesting," http://www.synthes.com/MediaBin/SUSA/SUBRORIAJ8968b.PDF 2008, pp. 1-8.
(Continued)

*Primary Examiner* — Adam Marcetich
(74) *Attorney, Agent, or Firm* — Mark Malek; Stephen Bullock; Widerman Malek, PL

(57) ABSTRACT

The present invention provides for the harvesting of specific materials in multiple stages of filtration of bone graft materials from a reaming device, specifics of interconnected stages, related filtration materials, and techniques. The harvesting process collects large material in a first stage, and other materials of a limited geometric size in at least a
(Continued)

second stage of filtration. Such material captured in the second stage may contain plasma, cellular elements including stem cells as well as growth factors and other particulate matter of a specific geometrically limited size, using various filtration approaches including centrifugation in some embodiments. Further embodiments of the invention provide for an improved tubing interface and management approach to ease use in the operating room. Filtration materials may include biodegradable-material based filters and may allow direct implantation of small scale and larger scale matter in specific portions within the biodegradable-material itself.

18 Claims, 7 Drawing Sheets

Related U.S. Application Data

(60) Provisional application No. 61/326,234, filed on Apr. 21, 2010.

(51) Int. Cl.
- *A61K 35/28* (2015.01)
- *A61B 17/00* (2006.01)
- *A61B 10/02* (2006.01)

(52) U.S. Cl.
CPC ........... *A61K 35/28* (2013.01); *A61M 1/0001* (2013.01); *A61B 10/0283* (2013.01); *A61B 2010/0258* (2013.01); *A61B 2017/00004* (2013.01); *A61B 2017/00969* (2013.01); *A61M 2202/005* (2013.01); *A61M 2202/0014* (2013.01); *A61M 2202/0021* (2013.01); *A61M 2202/10* (2013.01); *A61M 2210/02* (2013.01)

(56) References Cited

U.S. PATENT DOCUMENTS

| | | | | |
|---|---|---|---|---|
| 6,013,853 | A * | 1/2000 | Athanasiou | A61F 2/0811 424/423 |
| 6,071,284 | A * | 6/2000 | Fox | A61B 10/0233 606/102 |
| 6,299,763 | B1 * | 10/2001 | Ashman | A61C 1/0076 210/448 |
| 6,325,806 | B1 * | 12/2001 | Fox | A61B 10/0233 606/102 |
| 6,387,070 | B1 * | 5/2002 | Marino | A61B 17/32002 210/256 |
| 6,783,532 | B2 | 8/2004 | Steiner et al. | |
| 7,008,394 | B2 | 3/2006 | Geise et al. | |
| 7,011,852 | B2 | 3/2006 | Sukavaneshvar et al. | |
| 7,832,566 | B2 | 11/2010 | Leach et al. | |
| 8,382,836 | B2 | 2/2013 | Hoerger et al. | |
| 2003/0161816 | A1 * | 8/2003 | Fraser | C12N 5/0667 424/93.7 |
| 2003/0190257 | A1 * | 10/2003 | Halstead | A61B 1/123 422/28 |
| 2003/0208181 | A1 * | 11/2003 | Geise | A61M 1/0236 604/406 |
| 2005/0139532 | A1 * | 6/2005 | Hershberger | A61M 1/0001 210/136 |
| 2006/0213374 | A1 * | 9/2006 | Shippert | A61M 1/0062 99/472 |
| 2006/0270974 | A1 * | 11/2006 | Goff | A61M 1/0056 604/93.01 |
| 2007/0055282 | A1 | 3/2007 | Muschler | |
| 2008/0243029 | A1 * | 10/2008 | Howard | A61B 17/1635 600/565 |
| 2010/0055078 | A1 * | 3/2010 | Hughes-Fulford | A61L 27/225 424/93.7 |

OTHER PUBLICATIONS

Synthes Ltd. "Reamer/Irrigator/Aspirator (RIA). For intramedulary reaming and bone harvesting," Technique Guide, www.synthes.com/reprocessing, Jul. 2008. (37 pages).

* cited by examiner

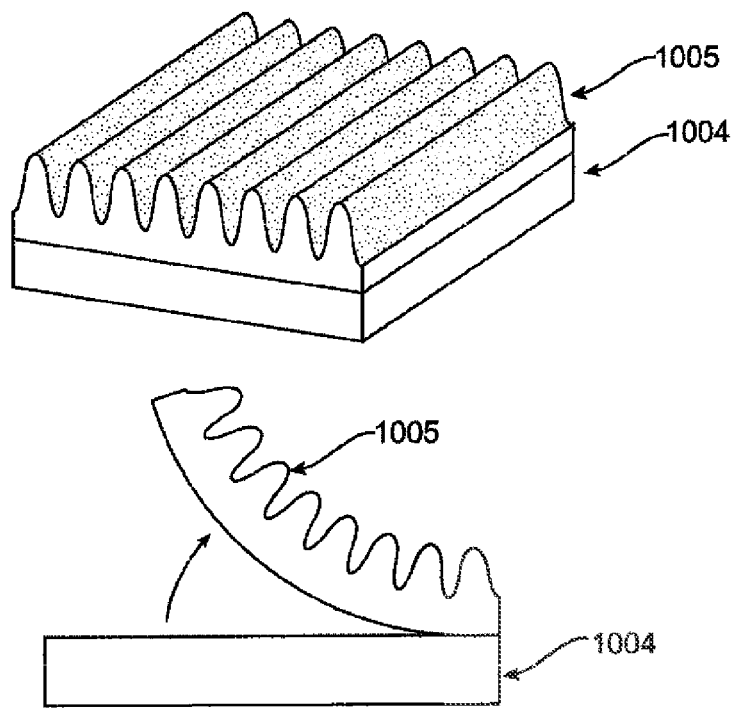
FIG. 11
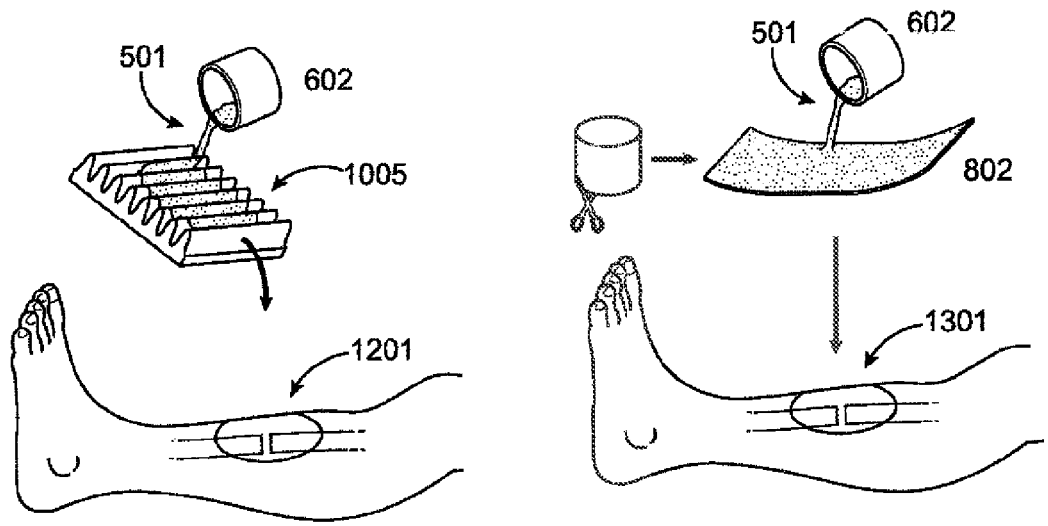
FIG. 12
FIG. 13

APPARATUS FOR HARVESTING IMPROVED BONE GRAFT MATERIAL UTILIZING AN IMPLANTABLE BIODEGRADABLE FILTER

CROSS REFERENCE TO RELATED APPLICATION

The present application is a continuation of U.S. patent application Ser. No. 13/091,123 titled Apparatus, System, and Method for Harvesting Improved Bone Graft Material with Reamer-Irrigator-Aspirator (RIA) Device filed on Apr. 21, 2011, which, in turn, claimed priority to U.S. Provisional Patent Application Ser. No. 61/326,234, filed on Apr. 21, 2010, titled Apparatus, System, and Method for Harvesting Improved Bone Graft Material with Reamer-Irrigator-Aspirateor (RIA) Device, the entire contents of each of which are hereby incorporated into this application by reference to provide continuity of disclosure.

FIELD OF THE INVENTION

The present invention is in the technical field of medical devices. More particularly, the present invention is in the technical field of harvesting bone graft materials using a reamer device.

BACKGROUND OF THE INVENTION

Currently, materials in the output stream from a reaming device, such as the Reamer-Irrigator-Aspirator provided by Synthes, are not fully and efficiently collected. While there have been some attempts to collect large scale material, other materials such as plasma, and other cellular elements are not currently collected and are discarded. Further, the approach used even to collect the large scale materials, essentially bone fragments, is not efficient for medical personnel to use in the operating room.

SUMMARY OF THE INVENTION

It is an object of this invention to provide for an improvement in the collection of bone graft or other materials from the output of a reamer-irrigator-aspirator device. It is a further object of this invention to provide for an improved tubing interface and management approach to ease use in the operating room. It is a further object of this invention to provide for an improved "stage 1" or large scale matter filtering system to retrieve bone fragments and other large scale matter from the output of the RIA device. It is a further object of this invention to provide for a second stage filtration or separation approach to separate the remaining small scale matter, including but not limited to cellular elements, from the irrigation water following the stage 1 filtration system. The current invention operates with a RIA device to provide a filtration approach to retrieve matter which is useful during bone graft harvesting and other procedures. The RIA device reams a bone such as a femur. The RIA device is connected to an improved hosing system where a bi-lumen hose allows for easier management of the hosing in the operating room. One tube of the bi-lumen hosing provides water to the RIA to perform irrigation. The other hose receives the output of the RIA, which consists of water, large scale matter, and small scale matter including cellular elements in some embodiments. The large scale matter has a significant amount of bone fragments. The small scale matter contains a significant amount of plasma, stem cells, marrow material, and further additional elements which may include growth factors, depending on the porosity of the filter mechanism. The tube receiving the waste is connected to the stage 1 filter which filters out the stage 1 material. The filter in this case is a re-usable mesh or porous filter plate. The plate may be removed, and the collected stage 1 material used for bone grafts, or other uses. The output of the stage 1 filter is passed via another tube in one embodiment to a stage 2 filter or separator. Such a separator may be another filtering mechanism, or a centrifuge type device. When a centrifuge is used, a filter is used to remove the stage 2 material. This filter may be made of collagen, such that after collection of the stage 2 materials, the cylindrical collagen filter may be removed from the centrifuge, cut open, and laid flat on a stage 2 material pad. This pad may be combined with the stage 1 material, and used directly in the body for the grafting process, as collagen will dissolve at a later time. The alternative stage 2 filtration approach is to use a filter box, with a collagen filter. In another embodiment, a plurality of filters may be used, each targeted at retaining particulate matter of a desired geometry. In such cases any combination of porosities of each pair of filter stages may be utilized such that a specific range of particulate size is retained in the stage 2 filter or subsequent combination of any two cascaded filters.

BRIEF DESCRIPTION OF THE DRAWINGS

FIG. 11 shows the collagen filter being removed from the stage 2 filter, for use of the retained stage 2 materials.

FIG. 12 shows stage 1 material in one embodiment being added to the stage 2 materials on a collagen filter, pad, or sponge and use as part of a bone graft in a patient. In this case the collagen filter, or sponge would be placed inside the patient along with the stage 1 and stage 2 materials, which may be modified in proportions. The filter, in one embodiment, would dissolve at a later time.

FIG. 13 shows an alternative embodiment of stage 1 materials being added to the stage 2 materials on a collagen filter, pad, or sponge and use as part of a bone graft in a patient.

Note that the specific examples provided are not intended to be limiting but are specific embodiments of the invention. Various alternative materials and processes may be used as known in the art.

DETAILED DESCRIPTION OF THE INVENTION

Figure 1A:
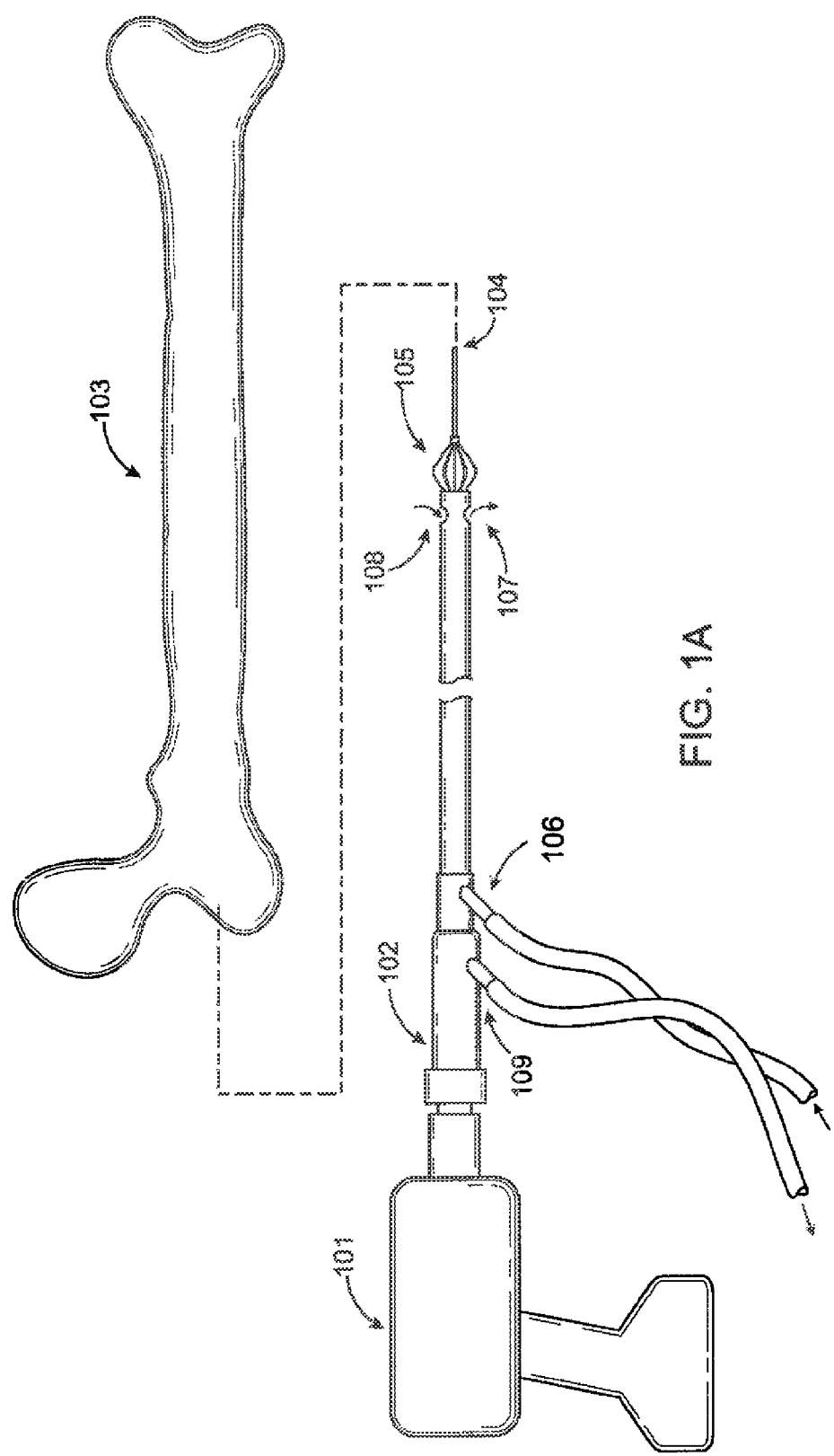
FIG. 1A is a diagram of the prior art RIA device.
Figure 1B:
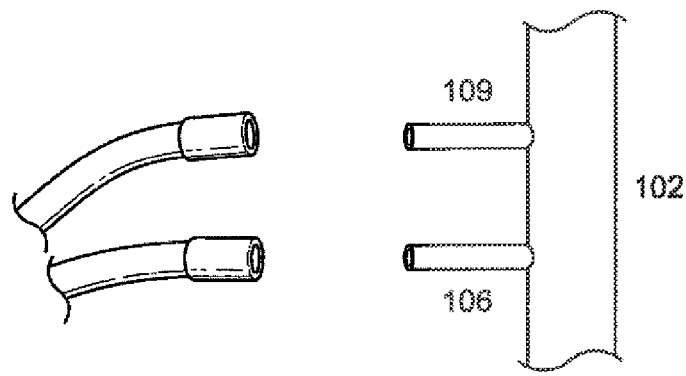
FIG. 1B is a diagram of the prior art RIA device tubing interface.

Referring to FIG. 1A, the depiction of the RIA which stands for Reamer Irrigator Aspirator. Depicted is a power source 101, a drill of any variety used within the operating room. The RIA device 102 which is designed as a medullary bone graft harvesting device. The bone graft material would be harvested from the medullary canal of a native human femur 103 using the RIA device 102. A guide wire 104 is inserted into the medullary canal providing a guide for the RIA device 102 to remain within the medullary canal. The reamer head 105 is designed to cut the bone that is currently being harvested by the device. Through Port 106, the entry portal, saline is pumped into the device exiting out of Port 107. Suction is applied to the device through Port 109, providing an avenue for fluid as well as bone graft material to exit the medullary canal via Port 108. It is then tunneled through Port 109 to a collection device or to the waste suction canister within the operating room. FIG. 1B is a depiction of the current device in larger scale at the region where the suction as well as irrigation ports meet with the RIA device 102. The RIA device with Port 106, labeled 102, is the port allowing for saline to float within the device and Port 109 being the port providing suction and an avenue for the evacuation of material from the medullary canal.

Figure 2:
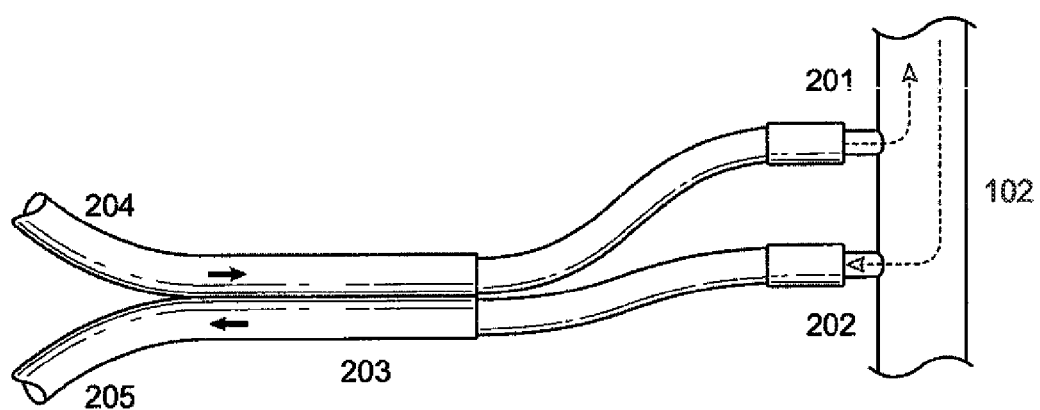
FIG. 2 shows the bi-lumen tube conned to a tube port in a RIA or other device.

FIG. 2 is a depiction of the improved tubing system in one embodiment of this current invention. Depicted is the RIA device 102 with modified coupling Zones 201 as well as 202. 201 would be the coupling point for saline inflow into the RIA device 102; whereas, Port 202 would provide for efflux and evacuation of fluid as well as bone graft material that is applied via suction. The suction source would be obtained through a source available within the operating room. The tubing is coupled 203 to provide for less entanglement and more streamlined use within the operating room. These tubes would branch allowing for filtration/separation canisters, to be described later. Tube 204 would provide an inflow source for saline whereas Tube 205 would provide suction as well as an egress pathway for bone graft as well as saline or other fluids.

Figure 3:
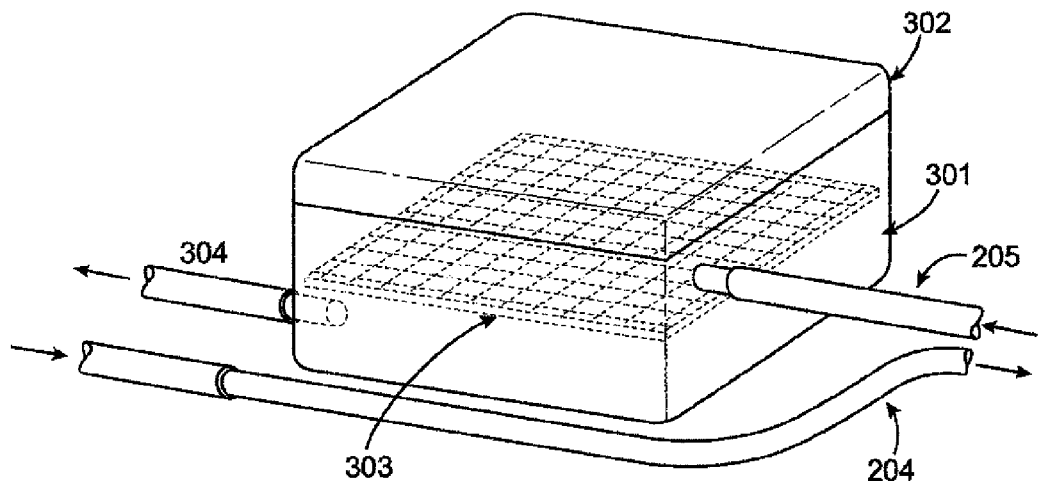
FIG. 3 shows the improved stage 1 filter with the water irrigation hose bypassing the filter (not integrated).

FIG. 3 depicts an embodiment of a modified Stage 1 filter for the collection of materials from the harvesting site. Saline and bone graft material would flow into the device via Tube 205. The device container, 301, would contain a hinged lid 302. Within the container 301, would be a Removable Porous Filter Device, 303, that is porous in nature to capture large bone graft material but provide for the flow through of saline, blood products, plasma, cells, and growth factors, and other particulate matter of a specific geometrically limited size. The material would be drawn through the filter via suction applied through Port 304. Also depicted in FIG. 3 would be Tubing 204 that would allow for saline to flow to the RIA device 102 and provide irrigation to facilitate the evacuation of bone graft material.

Figure 4:
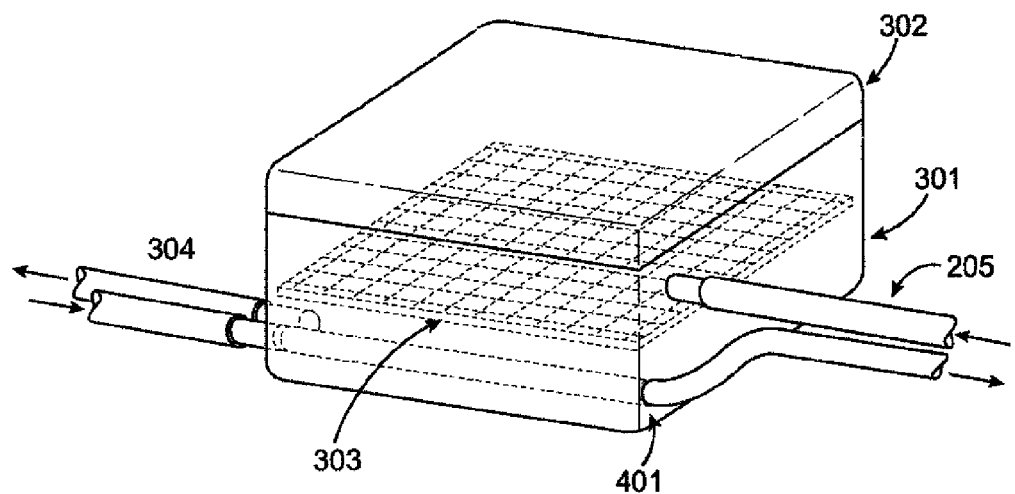
FIG. 4 shows the Stage 1 filter with an integrated pass through irrigation source hose for use with the bi-lumen tubing.

FIG. 4 is an alternative embodiment of the Stage 1 filter. Tube 401 would be contained within the Filter Device container, 301, once again avoiding significant entanglement and providing for more efficient use within the operating room. The remaining portion of the device would function very similar as the device in FIG. 3. A hinged lid, 302, providing access to Porous Filter 303, would catch material entering via Port 205 once again allowing for saline, blood products, plasma, cells, growth factors and other particulate matter of a specific geometrically limited size to pass through and be drawn out via Port 304.

Figure 5:
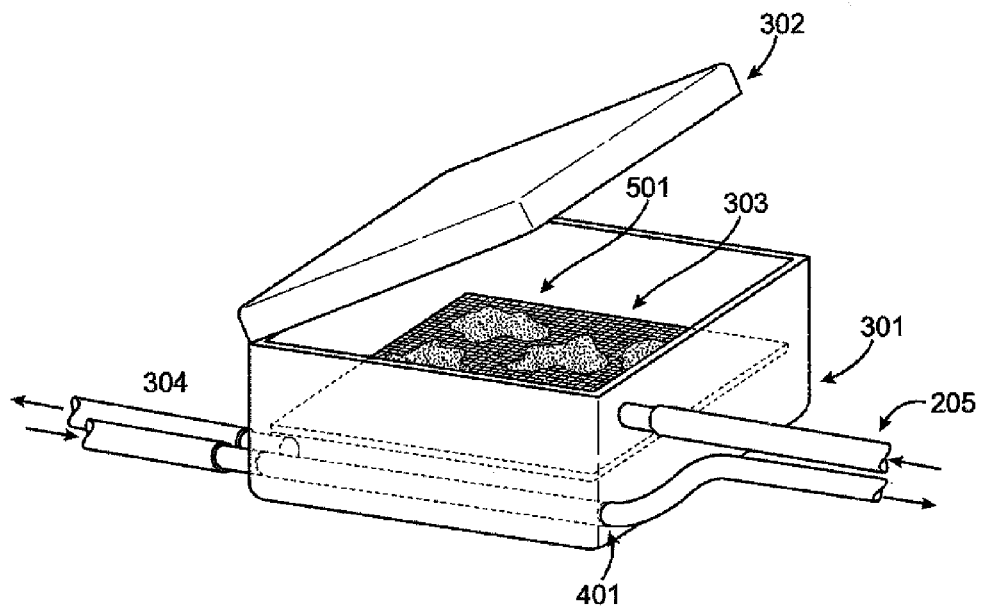
FIG. 5 shows the stage 1 filter with the lid open, and stage 1 material inside.

FIG. 5 shows one depiction of the initial stage filter with additional details noted. Through Tube 205 saline as well as graft material evacuated from the medullary canal would enter Stage 1 container 301. The lid now hinged open, depicted at 302, allows for access to Removal Filter 303 containing Bone Graft Material 501. The remaining portion of the fluid, containing blood products, plasma, cells, growth factors and other particulate matter of a specific geometrically limited size would be evacuated via suction, through Tube 304.

Figure 6:
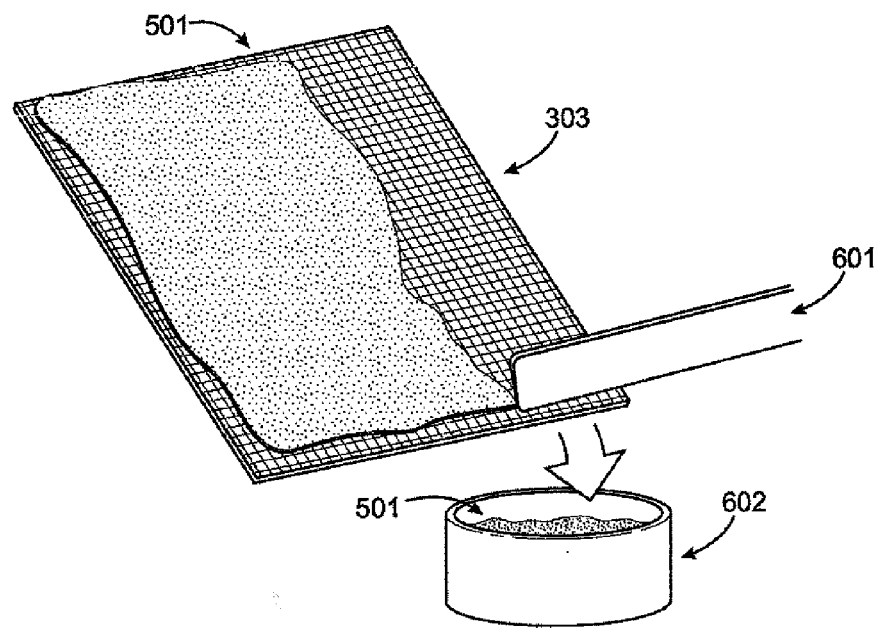
FIG. 6 shows the removed filter plate from the stage 1 filter with the stage 1 material being collected from the filter plate into a canister for later use.

FIG. 6 depicts the removal of the material off of Porous Filter 303. Bone Graft Material 501 would then be removed via Spatula Device 601 into Container 602. These Devices, 601 as well as 602, would be sterile and used within the operative field. The Collection Container 602 provides for a sterile container to contain the Bone Graft Material 501 for later re-implantation at the desired clinical site.

Figure 7:
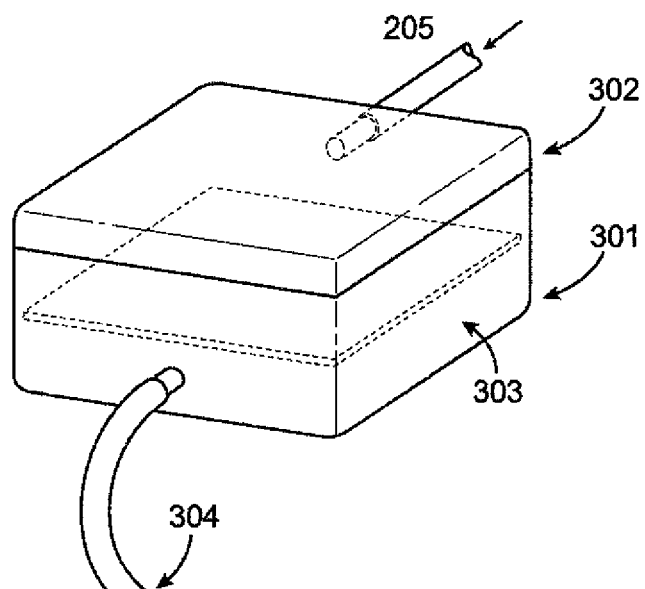
FIG. 7 shows the stage 1 filter connected to a stage 2 collector centrifuge, with a collagen sponge or filter cylinder inside in one embodiment of the invention.

FIG. 7 represents one embodiment of the second stage filtration system which would be designed to remove excess water yet retain additional graft material including but not limited to blood products, plasma, cellular bone marrow/stem cell elements, as well as growth factors and other particulate matter of a specific geometrically limited size. Depicted in FIG. 7 is the initial Stage Filter 303 contained within the Filtration container 301 covered by Lid 302. Initial material harvested from the RIA device 102 would enter the container via Tube 205. Large bone graft material would be trapped by Filter 303 allowing for the pass through/flow through of the remaining material through Tube 304. This material once again would represent blood products, plasma, and cellular elements including stem cells as well as growth factors and other particulate matter of a specific geometrically limited size. This material would then enter Centrifugal Filtration Device 701. This device would contain a porous filtration capturing membrane 801. It will be covered and contained within the centrifugal filtration device via Lid 703. The porous filtration capturing membrane 801 would be porous in its design to allow for capturing of blood products, plasma, cellular elements/stem cells, as well as growth factors and other particulate matter of a specific geometrically limited size, yet provide for the separation of fluid. This separation would then allow for a concentration of the graft elements and further to extract fluid from the system via centrifugation. The fluid may exit via Tubing 702 connected to an evacuation port in the various embodiments of the second stage filter as illustrated, for example, in FIG. 7.

Figure 8:
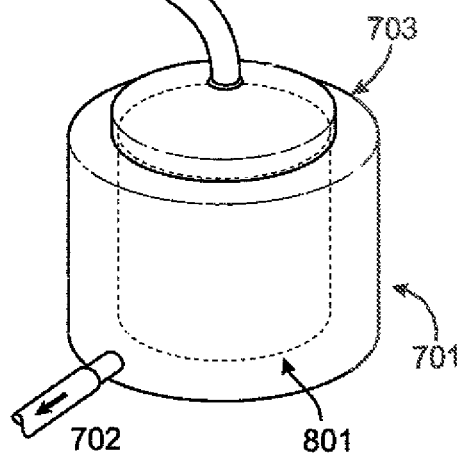
FIG. 8 shows the collagen filter removed from the centrifuge after collection, then cut into a flat "pad" of stage 2 material on the collagen filter or sponge in one embodiment.
Figure 8:
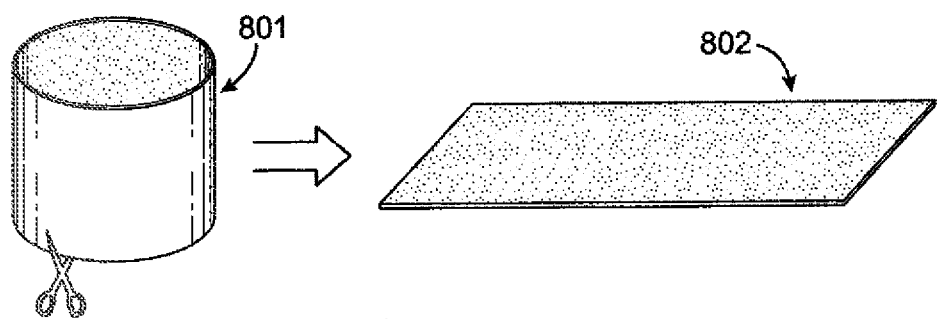

FIG. 8 is a detailed depiction of the porous filtration capturing membrane within the Filtration Device 701. The cylindrical porous filtration capturing membrane 801 would be removed from Centrifugal Filtration Device 701 and cut to provide for a rectangular surface 802 and function as a graft impregnated membrane for re-implantation within the patient.

Figure 9:
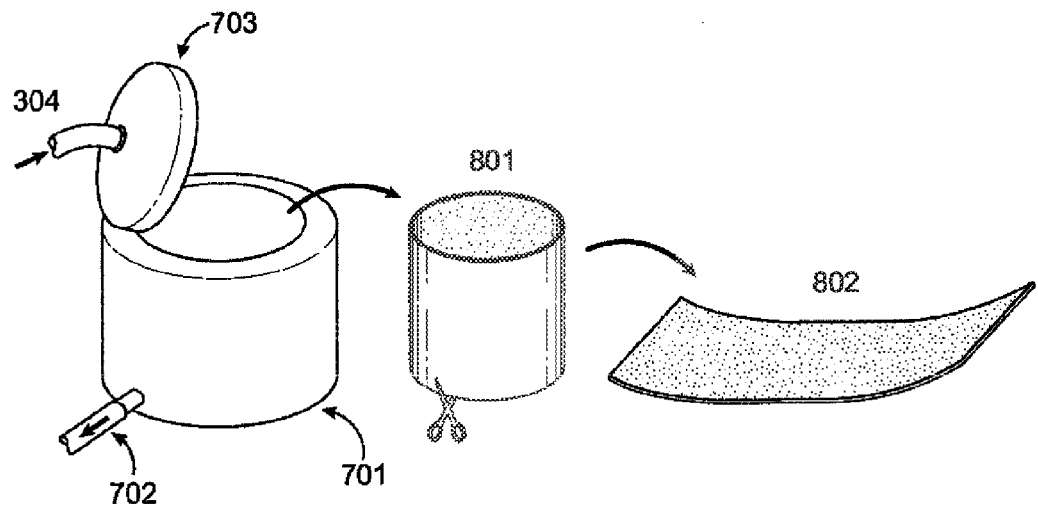
FIG. 9 shows the collagen or other filter material removed from the centrifuge, cut and laid flat as a stage 2 pad.

FIG. 9, once again, provides for a drawing of this process starting with the Centrifugal Filtration Device 701 that is sealed via Lid 703. Material filtered through the first stage filtration system enters via Tube 304. After a centrifugal filtration process takes place, within 701, the material is trapped within the porous filtration capturing membrane 801 which is porous in nature to provide for the capture of blood products, cellular elements including stem cells, as well as growth factors and other particulate matter of a specific geometrically limited size, but allow for the pass through of fluid that would exit via Tubing 702 connected to an evacuation port in the various embodiments of the second stage filter as illustrated, for example, in FIG. 9. The porous filtration capturing membrane 801 could then be cut to size and later implanted within the patient.

Figure 10:
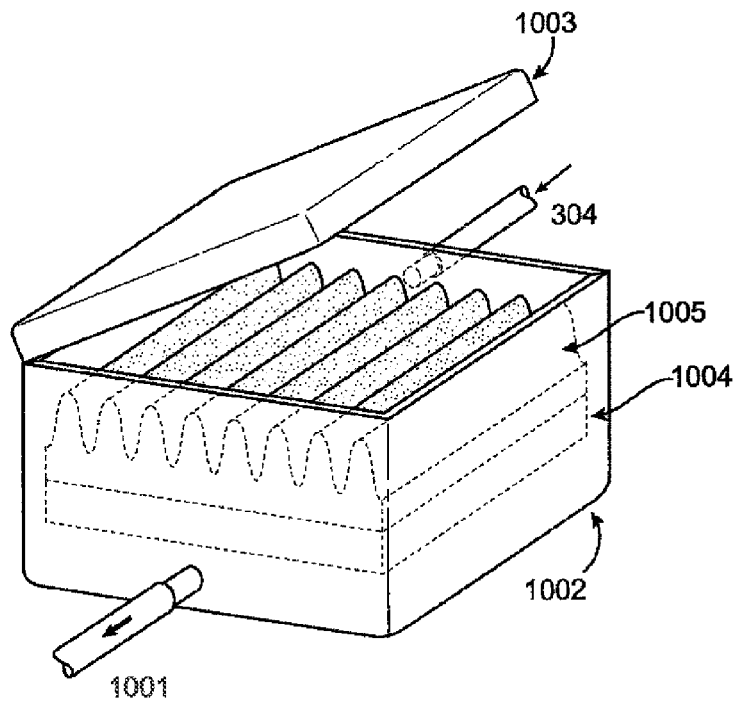
FIG. 10 shows an alternative stage 2 collector using a filtration system, containing a collagen or other materials filter plate or sponge.

FIG. 10 represents an alternative embodiment of the second stage filter. This filter would be designed for a more passive filtration process facilitated by vacuum negative pressure. Filtration Canister 1002 would contain a Hinged Lid 1003. Material exiting the first stage filter would enter the device via Tube 304. The undulating surface depicted as 1005 would be a filtration surface undulated for increasing surface area. It would reside on top of a porous yet Hydrophilic Membrane 1004 that would facilitate the extraction of fluid. The retention of blood products, plasma, cellular elements including stem cells, growth factors and other particulate matter of a specific geometrically limited size, would take place on the second stage (or any subsequent stage) filtration surface 1005. Excess fluid would then be evacuated via Tube 1001 connected to an evacuation port in the various embodiments of the second stage filter as illustrated, for example, in FIG. 10.

In FIG. 11 a more detailed depiction of the second stage filter and hydrophilic membrane is depicted. The undulating Second Stage Filter 1005 would initially lie on top of porous Hydrophilic Membrane 1004. The Filtration Surface 1005 would then be peeled away from hydrophilic/porous Surface 1004 after it has been exposed to the second stage graft/fluid material. This surface would then be available for implantation within the desired clinical setting.

FIG. 12 represents the final combination of material from the first as well as second stage of filtration, or any combination of a plurality of filtration stages. Material from the first stage of filtration, depicted as 501, and being contained within Sterile Container 602, would then be placed on top of Undulating Porous Sponge 1005. This would become a combination graft of large fragments of bone graft material from stage 1 combined with desired blood products, plasma, cellular elements/stem cells, growth factors and other particulate matter of a specific geometrically limited size. This combined graft can then be used in the desired clinical location. The location being depicted in FIG. 12 as 1201, a tibial bone graft site, although other site may be desired.

An alternative embodiment of the combined graft would be depicted in FIG. 13 that would provide for a combination of material from the first stage filtration as well as material captured via centrifugal filtration device and contained within the porous filtration capturing membrane 801. Material from the first stage of Filtration 501 would be removed from Container 602. It would then be placed on the cut porous filtration capturing membrane 801, which would contain blood products, plasma, cellular elements including stem cells as well as growth factors and other particulate matter of a specific geometrically limited size. This would then be made available for implantation within a desired clinical bone graft site depicted as a tibial site 1301 in FIG. 13, although other site may be desired.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

That which is claimed is:

1. A device for the collection of materials from a medullary bone graft source to be used with a reaming device, the apparatus comprising:
    a plurality of filters,
    a plurality of filter containers, and
    a plurality of connecting tubes,
    wherein an input of a first stage filter container of the plurality of filter containers containing a first stage filter of the plurality of filters is connected, by a first connecting tube, to an output of the reaming device, the reaming device utilizing an irrigation fluid supply and a suction source,
    wherein a flow of materials harvested by the reaming device and suspended in the irrigation fluid passes through the first connecting tube,
    wherein the flow of materials suspended in the irrigation fluid is filtered by the first stage filter,
    wherein the first stage filter possesses a first particulate size selectivity to separate a first stage retained material from the flow of materials suspended in the irrigation fluid to provide a first stage output flow of materials suspended in the irrigation fluid,
    wherein the first stage output flow of materials suspended in the irrigation fluid is passed through an output of the first stage filter container,
    wherein an input of a second stage filter container of the plurality of filter containers is connected, by a second connecting tube, to the output of the first stage filter container,
    wherein the first stage output flow of materials suspended in the irrigation fluid is filtered by the second stage filter,
    wherein the second stage filter possess a second particulate size selectivity to separate a second stage retained material from the first stage output flow of materials suspended in the irrigation fluid to provide a second stage output flow of materials suspended in the irrigation fluid, and wherein the second stage particulate size selectivity includes particulate sizes less than those included with the first particulate size selectivity,
    wherein the second stage filter container includes an evacuation port to permit the flow of materials suspended in the irrigation fluid to be evacuated from the second stage filter container in a continuous process,
    wherein the continuous process includes the first stage filter container receiving an additional flow of materials suspended in the irrigation fluid from the first connecting tube simultaneously with the second stage filter providing the second stage output flow of materials suspended in the irrigation fluid to the evacuation port of the second stage filter container,
    wherein the second stage filter comprises a biocompatible filter material which is removable from the second stage filter container, and wherein the second stage filter is configured to receive at least a portion of the first stage retained material in combination with the second stage retained material to create a combined graft product.

2. The device of claim 1 wherein the reaming device is a reamer irrigator aspirator device.

3. The device of claim 1 wherein the first connecting tube is a bi-lumen connecting tube.

4. The device of claim 1 wherein the first particulate size selectivity allows for the collection of bone fragments, and allows for the passing of a significant portion of one or more of irrigation fluid, plasma, stem cells, growth factors, and cellular matter as the first stage output flow of materials suspended in the irrigation fluid.

5. The device of claim 4 wherein the second particulate size selectivity, allows for the collection of a significant portion of one or more of plasma, stem cells, growth factors, and cellular matter, and allows for the passing of a significant portion of the irrigation fluid, as the second stage output flow of materials suspended in the irrigation fluid.

6. The device of claim 1 wherein the second stage filter container comprises a centrifuge configured to separate at least a portion of the irrigation fluid from the second stage retained material during a continuous process utilizing a second stage filter container evacuation port.

7. The device of claim 5 wherein the second stage filter utilizes a collagen-based filter.

8. The device of claim 5, wherein the second stage filter utilizes a hydrophilic material aided by suction to separate the second stage retained material from the first stage output flow of material suspended in the irrigation fluid to provide the second stage output flow of material suspended in the irrigation fluid.

9. The device of claim 5 wherein the second stage filter comprises an undulated surface on top of a porous and hydrophilic membrane configured to retain the collected and reusable material in a shape geometrically consistent with the undulated surface of the second stage filter.

10. The device of claim 9 wherein the combined graft product is implantable into a patient.

11. The device of claim 1 wherein the biocompatible filter material is comprised of a material configured to be implanted into a human.

12. The device of claim 11 wherein the second stage filter is comprised of material configured to be biodegradable.

13. The device of claim 1 wherein the first stage filter container has a hinged lid.

14. The device of claim 13 wherein at least one of the plurality of connecting tubes does not pass through the first stage filter container.

15. The device of claim 13 wherein the plurality of connecting tubes passes through the first stage filter container.

16. The device of claim 1, wherein a single integrated structure comprises two or more of the plurality of filter containers.

17. The device of claim 16, wherein the single integrated structure further comprises one or more of the plurality of connecting tubes.

18. A multi-staged filter device for use in producing an implantable combined bone graft product, the multi-staged filter apparatus comprising:
a biocompatible material-based substrate,
a first stage filter container of a plurality of filter containers, and
at least one second stage filter container of the plurality of filter containers,
wherein a reaming device is used to collect materials from a medullary bone graft source and provide a flow of materials suspended in irrigation fluid,
wherein an input of the first stage filter container of the plurality of filter containers containing the first stage filter of the plurality of filters is connected, by a first connecting tube, to an output of the reaming device,
wherein the flow of materials suspended in the irrigation fluid passes through the first connecting tube,
wherein the flow of materials suspended in the irrigation fluid is filtered by the first stage filter,
wherein the first stage filter possesses a first particulate size selectivity to separate a first stage retained material from the flow of materials suspended in the irrigation fluid to provide a first stage output flow of materials suspended in the irrigation fluid,
wherein the first particulate size selectivity allows for the collection of bone fragments, and allows for the passing of a significant portion of one or more of irrigation fluid, plasma, stem cells, growth factors, and cellular matter as the first stage output flow of materials suspended in the irrigation fluid,
wherein the first stage output flow of materials suspended in the irrigation fluid is passed through an output of the first stage filter container,
wherein an input of the second stage filter container of the plurality of filter containers containing the second stage filter of the plurality of filters is connected, by a second connecting tube, to the output of the first stage filter container,
wherein the first stage output flow of materials suspended in the irrigation fluid is filtered by the second stage filter,
wherein the second stage filter possess a second particulate size selectivity to separate a second stage retained material from the first stage output flow of materials suspended in the irrigation fluid to provide a second stage output flow of materials suspended in the irrigation fluid, and wherein the second stage particulate size selectivity includes particulate sizes less than those included with the first particulate size selectivity,
wherein the second particulate size selectivity allows for the collection of a significant portion of one or more of plasma, stem cells, growth factors, and cellular matter, and allows for the passing of a significant portion of the irrigation fluid, as the second stage output flow of materials suspended in the irrigation fluid,
wherein the second stage filter container includes an evacuation port to permit the flow of materials suspended in the irrigation fluid to be evacuated from the second stage filter container in a continuous process,
wherein the continuous process includes the first stage filter container receiving an additional flow of materials suspended in the irrigation fluid from the first connecting tube simultaneously with the second stage filter providing the second stage output flow of materials suspended in the irrigation fluid to the evacuation port of the second stage filter container,
wherein the second stage filter comprises the biocompatible material-based substrate,
wherein the biocompatible material-based substrate is comprised of:
a disposable biocompatible material-based portion having dimensions compatible with the second stage filter container, and
a selectable and implantable biocompatible material-based portion capable of being adjusted to selectable dimensions compatible with the requirements of a specific patient, and to the exclusion of the disposable biocompatible material portion, wherein the second stage filter, including said biocompatible material-based substrate, is removable, and wherein the selectable and implantable biocompatible material-based portion of said second stage filter is further configured to receive at least a portion of the first stage retained material in combination with at least a portion of the second stage retained material to create a combined graft product.

* * * * *